Figure 1:
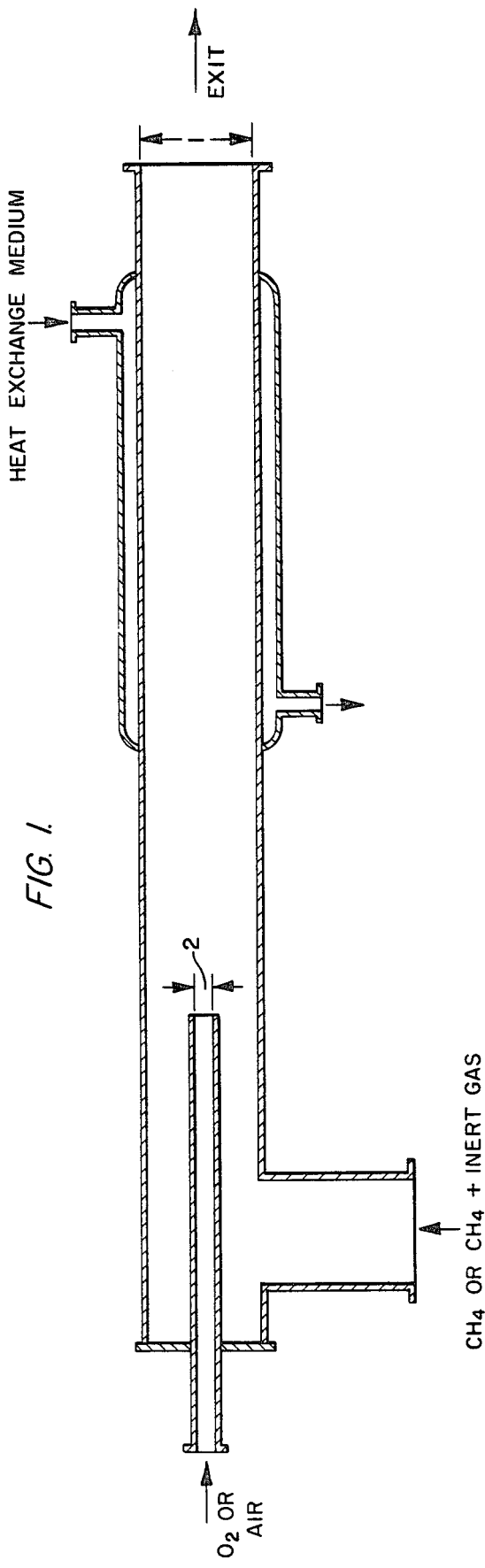

United States Patent [19]

Brockhaus et al.

[11] 4,243,613
[45] Jan. 6, 1981

[54] PROCESS FOR THE MANUFACTURE OF MIXTURES OF FORMALDEHYDE AND METHANOL BY PARTIAL OXIDATION OF METHANE

[75] Inventors: Rudolf Brockhaus, Marl; Hans-Jürgen Franke, Dorsten, both of Fed. Rep. of Germany

[73] Assignee: Chemische Werke Hüls Aktiengesellschaft, Fed. Rep. of Germany

[21] Appl. No.: 945,397

[22] Filed: Sep. 25, 1978

[30] Foreign Application Priority Data

Sep. 24, 1977 [DE] Fed. Rep. of Germany ....... 2743113

[51] Int. Cl.$^3$ ..................... C07C 47/48; C07C 27/14
[52] U.S. Cl. ..................................... 568/482; 568/910
[58] Field of Search ........................... 260/606, 604 R; 568/910

[56] References Cited

U.S. PATENT DOCUMENTS 2,722,553  11/1955  Mullen et al. ...................... 260/606

FOREIGN PATENT DOCUMENTS

| | | | |
|---|---|---|---|
| 1159421 | 12/1963 | Fed. Rep. of Germany | 260/604 R |
| 1217353 | 5/1966 | Fed. Rep. of Germany | 260/604 R |
| 2201429 | 7/1976 | Fed. Rep. of Germany | 260/604 R |
| 1056513 | 1/1967 | United Kingdom | 260/604 |
| 1410709 | 10/1975 | United Kingdom | 260/604 R |

OTHER PUBLICATIONS

Ullmann's Encyclopedia of Industrial Chemistry, 3rd Edition (1956), vol. 7, p. 663.

*Primary Examiner*—Werren B. Lone
*Attorney, Agent, or Firm*—Craig & Antonelli

[57] ABSTRACT

A continuous process for the partial oxidation of methane to produce mixtures of formaldehyde and methanol wherein methane and an oxidizing gas are reacted in a reaction zone in the form of a flame and the resulting reaction mixture is cooled followed by separation of the resulting products, is further improved by controlling the velocity of the oxidizing gas so that it is 50 to 300 meters per second higher than the methane gas with the methane gas being introduced in a velocity of from 1 to 15 meters per second. Also, the stream of methane gas has a volume that is 3 to 100 times greater than the volume of the stream of oxidizing gas introduced into the reaction zone.

10 Claims, 2 Drawing Figures

PROCESS FOR THE MANUFACTURE OF MIXTURES OF FORMALDEHYDE AND METHANOL BY PARTIAL OXIDATION OF METHANE

This invention relates to the production of formaldehyde and methane and, in particular, to a process for effecting the partial oxidation of methane to produce mixtures of formaldehyde and methanol.

Numerous publications relating to the oxidation of methane to formaldehyde are known from the prior art. In the case of processes carried out on an industrial scale, the obtaining of economic yields still presents considerable difficulties.

Because of the low reactivity of methane, temperatures of more than 1,000° C. are required to initiate the reaction, but at these temperatures the formaldehyde formed, and also other desired products, for example methanol, are unstable.

The addition of nitrogen oxides as a catalyst enables the reaction temperature to be lowered to 500° to 700° C. (*Ullmanns Enzyklopadic der Technischen Chemic*) [*Ullmann's Encyclopedia of Industrial Chemistry*], 3rd edition (1956), volume 7, page 663; DT-AS No. 1,217,353, corresponding to British Pat. No. 1,056,513; and German Pat. No. 1,159,421. However, these processes have not been able to find acceptance since additional material costs result from the high consumption of nitrogen oxides and, because of the aggressive nature of these compounds, increased expenditure on the technical equipment for the plant is required.

A process for the partial oxidation of hydrocarbons, in which the hydrocarbons are passed into hot, oxygen-containing combustion gases, is known from U.S. Pat. No. 2,722,553. The reaction takes place in an elongated chamber at high flow velocities. The stream of gas which leaves the reaction zone is chilled. Formaldehyde is obtained from this process only when "natural gas" is used, and it must be taken into account that natural gas consists mainly of $C_3$- and $C_4$-hydrocarbons. When methane is used, only synthesis gas is obtained.

A process for the partial oxidation of methane to formaldehyde and methanol is known from DT-AS No. 2,201,429 which corresponds to British Pat. No. 1,410,709. In this process, methane and oxidizing gas, which are under a pressure of 5 to 62 bars and preferably 20 to 52 bars, are allowed to flow together after methane and optionally the oxidizing gas have been heated separately to temperatures of 300° to 600° C. and the gas mixture is reacted, with self-ignition, in a reaction zone in the form of a flame, with an average residence time of $0.5 \times 10^{-3}$ to $5 \times 10^{-3}$ and preferably of $1 \times 10^{-3}$ to $2 \times 10^{-3}$ seconds. The reaction mixture is then chilled and the resulting products are separated off in the conventional manner.

Although a considerable advance over the earlier state of the art is achieved with this process, it has, nevertheless, been found that even this process is still subject to certain disadvantages. Thus, it is difficult to maintain the short reaction times demanded reached by large amounts of cycle gas lowering the coursion per pass through the reactor and furthermore usable results are obtained with the process only when pure oxygen is used as the oxidizing gas.

The object of the present invention was to find a process which avoids these disadvantages and with which the use of air does not result in any substantial disabentages compared with the use of oxygen alone.

This object—the improvement of the process, described in our earlier British Pat. No. 1,410,709, which corresponds to the German Pat. No. 22 01 429—has been achieved by the process of this invention for the partial oxidation of methane to formaldehyde and methanol using oxygen or oxygen-containing oxdizing gases, which includes the steps of allowing methane or a methane/inert gas mixture and an oxidizing gas to flow together in a combustion tube under a pressure of >5 bars, especially >20 bars, after methane or the methane/inert gas mixture and optionally the oxidizing gas have been heated separately to 300° to 600° C., reacting the gas mixture in a reaction zone in the form of a flame by self-ignition, cooling the reaction mixture and separating the resulting products in a conventional manner, and is further characterized in that a stream of the oxidizing gas is fed concentrically into a stream of methane or a methane/inert gas mixture, the velocity of which, measured in the cylindrical section of the combustion tube, is 1 to 15 m. second$^{-1}$, the velocity of the oxidizing gas being 50 to 300 m.second$^{-1}$ higher than that of the methane or methane/inert gas mixture and the volume of the stream of methane gas being 3 to 100 times greater than that of the stream of oxidizing gas.

The difference between the velocities of the stream of methane gas and the stream of oxidizing gas fed concentrically to the methane stream should be 50 to 300 m.second$^{-1}$. When the difference in velocities is more than 300 m.second$^{-1}$, this difference can result in the removal of the flame from the oxidizing gas outlet and thus in the reaction being discontinued. When the difference in velocities is less than 15 m.second$^{-1}$, total oxidation takes place direct at the inlet point for the oxidizing gas and thus resulting in overheating.

A difference in velocities of 75 to 250 m.second$^{-1}$ is particularly advantageous because in this range a reaction zone is formed within the combustion tube in which the formation and conservation of the desired unstable intermediate products is ensured in the optimum manner and because the energy expended to produce the discharge velocities is acceptable in this range.

The stream of methane gas should have a velocity of 1 to 15 m.second$^{-1}$ in the cylindrical section of the combustion tube. Below 1 m.second$^{-1}$, the residence time of the desired products in the hot reaction zone becomes too long. Above 15 m.second$^{-1}$, the formation of a reaction zone can be disturbed and, furthermore, adverse methane conversions result. A velocity of the stream of methane of up to 4 m.second$^{-1}$ in the cylindrical section of the combustion tube is particularly advantageous, because the mass transfer and heat transfer are favorable at this velocity and favorable conversions can be achieved.

The oxidizing gas can be oxygen or mixtures of oxygen with gases which are inert under the reaction conditions, especially air. Depending on the pressure, the methane can also be diluted with inert gases; thus, for example, under 45 bars, a methane gas consisting of 15% of methane and 85% of nitrogen can still be reacted successfully with the oxidizing gas. Further dilution of the methane employed can be compensated by an increase in pressure.

With regard to the start of the reaction, the ratio of methane to oxygen or air is variable to a substantial degree, but when oxygen gas is used as the oxidizing agent, the amount of oxygen in the total gas mixture should be not less than 0.1% by volume and when air is used as the oxidizing gas the amount of air in the total gas mixture should be not less than 1% by volume.

As is known, the auto-oxidation of methane under high pressures, such as 14,200 bars, and temperatures of 400° C. results virtually exclusively in methanol. Under normal pressure, methane reacts with oxygen or oxygen-containing gases only at temperatures at which the oxidation products, formaldehyde and methanol, are unstable and rapidly react further to form carbon oxides. According to experience, increase in the pressure lowers the ignition temperature. At lower temperatures, the reaction does not pass through the formaldehyde and methanol stages so rapidly, so that there is a possibility of withdrawing these desired products from the total oxidation to carbon oxides, by discontinuing the reaction. In combination with the other process conditions, pressure of more than 5 bars make it possible to carry out a process with completely satisfactory results. Particularly advantageous results are achieved when the process is carried out with pure methane in a pressure range above 20 bars. The addition of inert gas to the methane enables the partial vapor pressure to be further lowered without the result becoming substantially poorer.

The pressure used, or the partial pressure of the methane, determines the product spectrum. The process according to the invention can be adjusted to suit particular demands as desired, by varying the pressure. Since formaldehyde is the more valuable reaction product, it has proved advantageous, with regard to conversion and yield, to carry out the process in a pressure range of 20 to 50 bars for the pure methane.

Under lower pressures, for example 13 bars, the proportion of formaldehyde to methanol in the resulting product mixture is about 4:1, but the yields of formaldehyde and methanol in total are less.

In the medium pressure range, for example 30 bars, the proportions of formaldehyde to methanol are 1:1 when conditions are favorable; under higher pressures, the formation of methanol predominates to an ever-increasing extent. In the present context, there is little point in increasing the pressure to over 60 bars in the case of pure methane, because the product is then virtually entirely methanol. However, when relatively large amounts of inert gas are added, this partial pressure can be exceeded without this resulting in the formation of methanol exclusively.

On the other hand, the extent to which total oxidation takes place decreases with increasing pressure, and it is possible correspondingly to increase the conversion. It is thus possible substantially to vary the process and to adapt it to given economic conditions.

Heat is supplied to the compressed gases, that is to say methane or methane/inert gas mixture and the oxidizing gas, before they are mixed. A a rule, methane gas and the oxidizing gas are pre-heated to 300° to 600° C. When oxygen alone is used as the oxidizing gas, only the methane is preheated before the gases are mixed, in order to avoid corrosion problems. The conversion can be influenced by the temperature of the gases employed. The best results were obtained when the cited temperature range was used, because secondary reactions of the reaction products, formaldehyde and methanol, are still largely avoided in this range.

With regard to the removal of heat, the ratio of methane or methane/inert gas employed to oxidizing gas employed is important. Only some of the methane gas supplied serves as a raw material for the reaction; a considerable proportion of the methane gas is used in the equipment as a coolant for direct cooling. The heat of reaction is distributed in this coolant, so that a special chilling step for the hot reaction gases is not required.

Nevertheless, it is reasonable to cool the gases as rapidly as possible, in order to prevent any further reactions with incompletely converted oxygen. For the same reason, it is appropriate to keep low the proportion of unconverted oxygen.

In general, the volume of the stream of methane gas should be 3 to 100 times greater than the stream of oxidizing gas. When the oxidizing gas used is air, values in the lower part of this range are preferably employed and the process is carried out with a stream of methane gas which is about 3 to 15 times greater than that of air, since the nitrogen in the air acts as an additional coolant, and when oxygen is used, values in the upper part of this range are preferably employed and the process is carried out with a stream of methane gas which is about 10 to 100 times greater than that of oxygen.

These limits apply for the economically feasible range. The process according to the invention can also be carried out outside the range described, as Example 1 1 shows. In this case, a very low methane conversion was obtained; this gives rise to good yields but demands high expenditure on the circulating stream of cycle gas. As recognized by those skilled in the art, similar shifts in the limits also arise when the process is carried out in the range of high pressures.

If the conversion of methane per gas pass are only relatively low, it is advisable to recycle part of the stream of gas which leaves the reaction zone, after separating off the reaction products, into the reaction zone as circulating gas. The yield of the desired products is not impaired by recycling circulating gas. In order to remove from the system the carbon oxides which necessarily are obtained, some of the gas which leaves the reaction zone must be removed as off-gas when the circulating gas procedure is employed. Under the conditions of oxidation with oxygen, for example, this off-gas contains 20 to 80% by volume of methane. The remainder consists in the main of carbon oxides, the ratio of $CO:CO_2$ being between 1:3 and 1:10 depending on the operating conditions. A gas of this composition is a high-quality heating gas. This is of importance for the economy of the process according to the invention, since the bulk of the methane occurring as natural gas is, in any case, used for heating purposes. It is thus possible first to subject methane intended for heating purposes to the process according to the invention, to convert some of the methane into the valuable reaction products and then to use the resulting valuable off-gas for heating purposes.

The process according to the invention is simple to carry out and the necessary expenditure on apparatus is low. The reaction gases are fed to a burner. Suitable burners are gas burners in general, in which the outer burner tube and the inner jet have a common axis, so that a symmetrical flame forms. The gases are fed to the burner without premixing. In the case of oxidation with oxygen gas, only the stream of methane gas, which consists of fresh methane gas and circulating methane gas, is pre-heated, while the stream of oxygen is left at room temperature. If the oxygen were also to be heated to the input temperature, it would be necessary to choose materials which are resistant to oxygen at temperatures up to about 500° C. Heating of the oxygen is superfluous, however, because the oxygen is supplied only in a relatively small amount. The lines for the supply of oxygen and the jet are appropriately made of stainless steel.

The advantages of the process according to the invention are, above all, that very good yields of the desired products are obtained even without maintaining extremely short reaction times. As a result of this, scaling-up to larger burners is made considerably easier, since the flow conditions claimed can be maintained easily even in larger burners.

EXAMPLES

Methane or a methane/inert gas mixture was reacted with oxygen or air under the conditions which can be seen from the Table. The temperature in the burner was measured at the gas exit of the burner. The velocity is calculated with the measured temperature behind the preheater, this temperature is 10° to 20° lower then the temperature in the reactor. Only the temperature of oxygen was estimated 400° K. The velocity is the velocity in the inlet tubes. After passing through the burner, the reaction product was cooled by indirect cooling (heat exchanger). The conversion and yield were determined by analyzing the liquid products condensed-out and the off-gas.

In Experiments 1 to 27, the burner used was a burner according to FIG. 1. The internal diameter of the reaction tube (1) and the internal diameter of the inner tube (2), which is used to supply the oxidizing gas, can be seen from the table. The track length, that is to say the distance from entry of the stream of oxidizing gas into the stream of methane gas to entry of the stream of gas into zone of the reaction tube cooled by the heat exchanger is 120 cm. The reaction tube was cooled via the exchanger with air.

Figure 2:
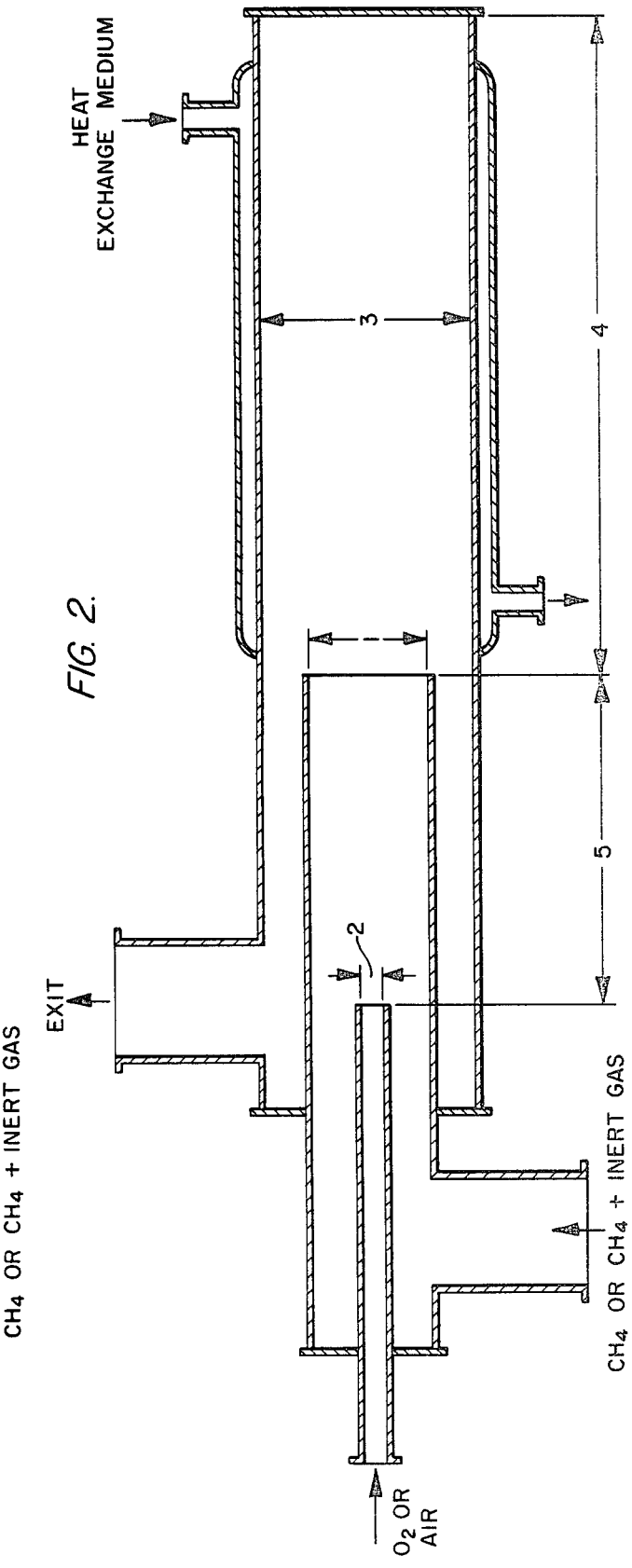

In Experiment 28, a burner with flow-reversal according to FIG. 2 is used: internal diameter of the so-called reaction tube (1)=30 mm, internal diameter of the inner tube, which is used to supply the oxidizing gas, (2)=0.7 mm, internal diameter of the slip-over tube (3)=53 mm, length of the slip-over tube from the end of the reaction tube to the seal of the slip-over tube (4)=90 cm. The distance of the $O_2$ or air lance from the end of the so-called reaction tube is 30 cm (5). Over the distance (4), the slip-over tube is cooled with air. The result can also be seen from the Table.

PART I

| Ex. | Reactor dimensions [mm] 1 | 2 | Pressure bars | Temperature in the reactor °C. | Amounts of gas employed [Nm³/h] Methane gas CH₄ | $N_2$ | oxidizing gas $O_2$ | air |
|---|---|---|---|---|---|---|---|---|
| 1 | 53 | 0.4 | 40 | 438 | 192 | — | 1.7 | — |
| 2 | 53 | 0.5 | 40 | 446 | 192 | — | 2.5 | — |
| 3 | 53 | 0.6 | 40 | 455 | 192 | — | 4.0 | — |
| 4 | 53 | 0.8 | 40 | 461 | 192 | — | 6.4 | — |
| 5 | 53 | 1.0 | 40 | 467 | 192 | — | 9.5 | — |
| 6 | 53 | 1.25 | 40 | 483 | 192 | — | 15.0 | — |
| 7 | 53 | 0.8 | 20 | 485 | 120 | — | 3.5 | — |
| 8 | 53 | 2.5 | 40 | 476 | 192 | — | — | 40 |
| 9 | 53 | 3.0 | 40 | 481 | 192 | — | — | 56 |
| 10 | 53 | 2.5 | 40 | 486 | 100 | 100 | — | 40 |
| 11 | 53 | 1.7 | 40 | 536 | 40 | 160 | — | 18 |
| 12 | 53 | 2.0 | 40 | 541 | 40 | 160 | — | 36 |
| 13 | 53 | 2.3 | 40 | 542 | 60 | 240 | — | 40 |
| 14 | 53 | 1.5 | 80 | 480 | 60 | 240 | — | 37 |
| 15 | 53 | 1.0 | 40 | 432 | 192 | — | 6.0 | — |
| 16 | 53 | 0.6 | 40 | 455 | 192 | — | 4.0 | — |
| 17 | 53 | 0.6 | 40 | 468 | 192 | — | 6.0 | — |
| 18 | 53 | 4.0 | 40 | 473 | 192 | — | — | 52 |
| 19 | 53 | 2.5 | 40 | 477 | 192 | — | — | 40 |
| 20 | 53 | 2.3 | 40 | 479 | 192 | — | — | 44 |
| 21 | 53 | 2.3 | 40 | 482 | 192 | — | — | 60 |
| 22 | 53 | 2.0 | 40 | 488 | 192 | — | — | 50 |
| 23 | 53 | 0.6 | 40 | 454 | 150 | — | 4.0 | — |
| 24 | 53 | 0.6 | 40 | 455 | 192 | — | 4.0 | — |
| 25 | 53 | 0.6 | 40 | 457 | 230 | — | 4.0 | — |
| 26 | 20 | 0.6 | 40 | 464 | 192 | — | 3.5 | — |
| 27 | 53 | 1.0 | 13 | 586 | 110 | — | 4.0 | — |
| 28 | 30/53 | 0.7 | 40 | 443 | 192 | — | 5.5 | — |

Part II

| Ex. | Methane volume Oxidizing gas volume | Velocity V [m. sec⁻¹] methane gas | oxidizing gas | ΔV | Conversion of CH₄ [%] |
|---|---|---|---|---|---|
| 1 | 112.9 | 1.5 | 133 | 131.5 | 0.50 |
| 2 | 76.8 | 1.5 | 125 | 123.5 | 1.04 |
| 3 | 48.0 | 1.6 | 139 | 137.4 | 2.10 |
| 4 | 30.0 | 1.6 | 125 | 123.4 | 2.90 |
| 5 | 20.2 | 1.6 | 119 | 117.4 | 4.00 |
| 6 | 12.8 | 1.6 | 120 | 118.4 | 6.10 |
| 7 | 34.3 | 2.0 | 137 | 135.0 | 1.90 |
| 8 | 4.8 | 1.6 | 150 | 148.4 | 4.00 |
| 9 | 3.4 | 1.6 | 147 | 145.4 | 5.60 |
| 10 | 5.0 | 1.7 | 152 | 150.3 | 6.10 |
| 11 | 11.1 | 1.8 | 158 | 156.2 | 5.90 |
| 12 | 5.6 | 1.8 | 229 | 227.2 | 9.80 |
| 13 | 7.5 | 2.7 | 193 | 190.3 | 8.90 |
| 14 | 8.1 | 1.3 | 194 | 192.7 | 9.10 |
| 15 | 32.0 | 1.5 | 75 | 73.5 | 2.20 |
| 16 | 48.0 | 1.6 | 139 | 137.4 | 2.10 |
| 17 | 32.0 | 1.6 | 208 | 206.4 | 2.20 |
| 18 | 3.7 | 1.6 | 76 | 74.4 | 4.00 |
| 19 | 4.8 | 1.6 | 150 | 148.4 | 4.00 |
| 20 | 4.4 | 1.6 | 196 | 194.4 | 4.20 |
| 21 | 3.2 | 1.6 | 268 | 266.4 | 4.30 |
| 22 | 3.8 | 1.6 | 297 | 295.4 | 4.20 |
| 23 | 37.5 | 1.2 | 139 | 137.8 | 2.40 |
| 24 | 48.0 | 1.6 | 139 | 137.4 | 2.10 |
| 25 | 57.5 | 1.9 | 139 | 137.1 | 1.60 |
| 26 | 54.9 | 11.1 | 122 | 110.9 | 2.45 |
| 27 | 27.5 | 3.24 | 150 | 146.8 | 2.21 |
| 28 | 34.9 | 1.5 | 140 | 138.5 | 2.14 |

Part III

| Ex. | Selectivity based on CH₄ converted [%] HCHO | CH₃OH | HCHOHCH₃OH | Yield based on CH₄ employed [%] HCHOHCH₃OH | HCHO |
|---|---|---|---|---|---|
| 1 | 22.85 | 68.55 | 91.4 | 0.457 | 0.114 |
| 2 | 18.76 | 67.54 | 86.3 | 0.897 | 0.195 |
| 3 | 17.04 | 59.64 | 76.7 | 1.611 | 0.358 |

-continued

Part III

| Ex. | Selectivity based on CH₄ converted [%] | | | Yield based on CH₄ employed [%] | |
|---|---|---|---|---|---|
|  | HCHO | CH₃OH | HCHOHCH₃OH | HCHOHCH₃OH | HCHO |
| 4  | 17.00 | 54.40 | 71.4 | 2.071 | 0.493 |
| 5  | 16.72 | 48.49 | 65.2 | 2.608 | 0.669 |
| 6  | 13.83 | 34.58 | 48.4 | 2.952 | 0.844 |
| 7  | 22.52 | 24.77 | 47.3 | 0.899 | 0.428 |
| 8  | 18.89 | 52.89 | 71.8 | 2.872 | 0.756 |
| 9  | 19.48 | 44.8  | 64.3 | 3.601 | 1.091 |
| 10 | 13.29 | 27.91 | 41.2 | 2.513 | 0.811 |
| 11 | 16.67 | 18.34 | 35.0 | 2.065 | 0.983 |
| 12 | 17.05 | 15.35 | 32.4 | 3.175 | 1.671 |
| 13 | 16.41 | 19.69 | 36.1 | 3.213 | 1.460 |
| 14 | 13.71 | 28.79 | 42.5 | 3.868 | 1.248 |
| 15 | 13.33 | 34.66 | 48.0 | 1.056 | 0.293 |
| 16 | 17.04 | 59.64 | 76.7 | 1.611 | 0.358 |
| 17 | 9.81  | 31.39 | 41.2 | 0.906 | 0.216 |
| 18 | 10.65 | 25.56 | 36.2 | 1.448 | 0.426 |
| 19 | 16.32 | 55.49 | 71.8 | 2.872 | 0.653 |
| 20 | 18.05 | 52.30 | 70.4 | 2.957 | 0.758 |
| 21 | 14.35 | 41.97 | 56.3 | 2.421 | 0.617 |
| 22 | 10.18 | 18.32 | 28.5 | 1.197 | 0.428 |
| 23 | 15.10 | 54.10 | 69.2 | 1.661 | 0.362 |
| 24 | 17.04 | 59.64 | 76.7 | 1.611 | 0.358 |
| 25 | 18.15 | 60.45 | 78.6 | 1.258 | 0.290 |
| 26 | 13.12 | 49.58 | 62.7 | 1.536 | 0.321 |
| 27 | 26.16 | 6.54  | 32.7 | 0.723 | 0.578 |
| 28 | 17.28 | 41.43 | 58.7 | 1.256 | 0.370 |

What is claimed is:

1. In a continuous process for the partial oxidation of methane to formaldehyde and methanol using oxygen or oxygen containing oxidizing gases, by allowing methane or a methane/inert gas mixture and oxidizing gas to flow together in a combustion tube under a pressure of more than 5 bars after the methane or the methane/inert gas mixture has been heated separately to 300° to 600° C., reacting the gas mixture resulting from the combination of said gases in a reaction zone of said combustion tube in the form of a flame by self-ignition at 300° to 600° C. to produce methanol and formaldehyde, cooling the reaction mixture and separating the resulting products, the improvement which comprises feeding the oxidizing gas concentrically into a stream of methane or a methane/inert gas mixture, the velocity of which, measured in the cylindrical section of the combustion tube, is 1 to 15 m. second$^{-1}$, the velocity of the oxidizing gas being 50 to 300 m. second$^{-1}$ higher than that of the methane or methane/inert gas mixture and the volume of the stream of methane gas being 3 to 100 times greater than that of the stream of oxidizing gas, said inert gas being a gas inert under the reaction conditions.

2. The process according to claim 1, wherein the velocity of the stream of oxidizing gas is 75 to 250 m. second$^{-1}$ higher than that of the stream of methane gas.

3. The process according to claim 1, wherein the methane and oxidizing gas are contacted at a pressure of from 10 to 120 bars in the reaction zone.

4. The process according to claim 1, wherein the oxidizing gas is heated separately to 300° to 600° C. before being combined and the temperature in the reaction zone ranges from 400° to 600° C.

5. The process according to claim 1, wherein the reaction mixture is cooled to a temperature of from 300° to 450° C.

6. The process according to claim 1, wherein a portion of the reaction mixture leaving the reaction zone is returned as a circulating gas after separating of condensable reaction products, said circulating gas being in a ratio of from 3:1 to 95:1 of the gases introduced into the reaction zone.

7. The process according to claim 1, wherein the inert gas consists essentially of nitrogen, carbon oxides with a ratio of CO:CO₂ being between 1:3 and 1:10, or a mixture thereof.

8. The process according to claim 1, wherein the inert gas consists essentially of nitrogen.

9. The process according to claim 1, wherein a stream of methane gas and a stream of an oxidizing gas consisting essentially of oxygen or air are reacted at a pressure of from 20 to 50 bars, the volume of a methane gas being about 3 to 15 times greater than that of the air oxidizing gas or the volume of the methane gas being about 10 to 100 times greater than that of the oxygen oxidizing gas.

10. The process according to claim 1, wherein a stream of methane and nitrogen is contacted with a stream of air.

* * * * *